(12) United States Patent
Ma et al.

(10) Patent No.: US 10,499,655 B2
(45) Date of Patent: Dec. 10, 2019

(54) REAGENTS AND METHODS FOR INHIBITING OR DISRUPTING BIOFILM

(71) Applicant: INSTITUTE OF MICROBIOLOGY, CHINESE ACADEMY OF SCIENCES, Beijing (CN)

(72) Inventors: Lvyan Ma, Beijing (CN); Shan Yu, Beijing (CN); Huijun Wu, Beijing (CN); Shiwei Wang, Beijing (CN); Di Wang, Beijing (CN)

(73) Assignee: INSTITUTE OF MICROBIOLOGY, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 15/557,812

(22) PCT Filed: Mar. 11, 2016

(86) PCT No.: PCT/CN2016/076171
§ 371 (c)(1),
(2) Date: Sep. 13, 2017

(87) PCT Pub. No.: WO2016/146037
PCT Pub. Date: Sep. 22, 2016

(65) Prior Publication Data
US 2018/0042243 A1 Feb. 15, 2018

(30) Foreign Application Priority Data

Mar. 13, 2015 (CN) .......................... 2015 1 0112746
Oct. 9, 2015 (CN) .......................... 2015 1 0648750

(51) Int. Cl.
*A01N 63/02* (2006.01)
*A01N 43/60* (2006.01)
*A61K 38/16* (2006.01)
*A01N 37/46* (2006.01)

(52) U.S. Cl.
CPC ............ *A01N 63/02* (2013.01); *A01N 37/46* (2013.01); *A01N 43/60* (2013.01); *A61K 38/164* (2013.01)

(58) Field of Classification Search
None
See application file for complete search history.

(56) References Cited

U.S. PATENT DOCUMENTS

| 9,480,729 | B2 | 11/2016 | Brumm | |
|---|---|---|---|---|
| 2008/0166753 | A1* | 7/2008 | Storey | C12Q 1/18 435/32 |
| 2013/0096078 | A1* | 4/2013 | Yoon | A61K 31/351 514/41 |

FOREIGN PATENT DOCUMENTS

WO 20150184526 A1 12/2015

OTHER PUBLICATIONS

Stover et al. "Complete genome sequence of Pseudomonas aeruginosa PA01, an opportunistic pathogen." Nature 406, 959-964, 2000.*
Byrd et al. Genetic and biochemical analyses of the Pseudomonas aeruginosa PsI exopolysaccharide reveal overlapping roles for polysaccharide synthesis enzymes in PsI and LPS production. Molecular Microbiology, Aug. 2009, vol. 73, No. 4, pp. 622-638.*
International Search Report for PCT/CN2016/076171 dated Jun. 14, 2016, 6 pages.
Written Opinion of the International Searching Authority for PCT/CN2016/076171 dated Jun. 14, 2016, 6 pages.
Yu, Shan et al.,"PsIg, a Self-Produced Glycosyl Hydrolase, Triggers Biofilm Disassembly by Disrupting Exopolysaccharide Matrix", Cell Research, vol. 25, No. 12, Dec. 31, 2015 (Dec. 31, 2015), pp. 1352-1367.
Byrd, M.S. et. al.,"Genetic and Biochemical Analyses of the Pseudomonas Aeruginosa PsI Exopolysaccharide Reveal Overlapping Roles for Polysaccharide Synthesis Enzymes in PsI and LPS Production", Molecular Microbiology, vol. 73, No. 4, Aug. 31, 2009 (Aug. 31, 2009), pp. 622-638.
Wang, Shiwei et al.; Coordination of Swarming Motility, Biosurfactant Synthesis, and Biofilm Matrix Exopolysaccharide Production in Pseudomonas aeruginosa, Appl Environ Microbial, 80:6724-6732, 2014.
Garima Sharma et al., Pseudomonas aeruginosa biofilm: Potential therapeutic targets, Biologicals, 42:1-7, 2014.
Wang, Shiwei et ai., The exopolysaccharide PsI-eDNA interaction enables the formation of a biofilm skeleton in Pseudomonas aeruginosa, Environmental Microbiology Reports, 7(2):330-340, 2015.
Perrin Baker et al., Exopolysaccharide biosynthetic glycoside hydrolases can be utilized to disrupt and prevent Pseudomonas aeruginosa biofilms, doi: http://dx.doi.org/10.1101/032714, 2016.
First Office Action in Chinese Application No. 201510648750.4 dated Apr. 11, 2019, 9 pages.

\* cited by examiner

*Primary Examiner* — Maury A Audet
(74) *Attorney, Agent, or Firm* — Metis IP LLC

(57) ABSTRACT

The present disclosure provides an inhibitor for inhibiting or disrupting biofilm and use thereof. Specifically, the present disclosure an application of a PsIG protein and a coding sequence thereof in inhibiting or disrupting a biofilm of a microorganism. The present disclosure also provides a composition and a preparation containing the PsIG protein to inhibit or disrupt a biofilm of a microorganism. The experiment shows that PsIG can effectively inhibit or disrupt a biofilm of *Pseudomonas* species, suggesting the great potential of PsIG in clinical and environmental fields.

19 Claims, 14 Drawing Sheets
Specification includes a Sequence Listing.

REAGENTS AND METHODS FOR INHIBITING OR DISRUPTING BIOFILM

CROSS-REFERENCE TO RELATED APPLICATIONS

This application is a U.S. national stage under 35 U.S.C. § 371 of International Application No. PCT/CN2016/076171, filed on Mar. 11, 2016, designating the United States of America, which claims priority to Chinese Patent Application No. 201510112746.6 filed on Mar. 13, 2015, and Chinese Patent Application No. 201510648750.4 filed on Oct. 9, 2015, the entire contents of which are incorporated herein by reference.

TECHNICAL HELD

The present disclosure generally relates to the field of microbial biotechnology. Specifically, the present disclosure relates to uses of a protein in inhibiting, disrupting or disassembling a biofilm of a microorganism.

BACKGROUND

"Biofilm" generally refers to communities of microorganism encased by extracellular polymeric substances, and is prevalent in natural, industrial, and clinical settings. Biofilms enhance survival, enabling organisms to adapt to changing conditions collectively instead of as single cells, and bring serious harm to human. For example, in medicine field, researches have indicated that about 65% human bacterial infections are related to biofilms, and antibiotics resistance of the microorganisms in the biofilms is hundreds or even thousands of times higher than that in a planktonic state, which greatly increases difficulties for clinical treatment.

Biofilm bacteria show extreme tolerance to almost all antibiotic classes. One of the most important features of biofilms is self-secreted extracellular polymeric substances consisting of mainly polysaccharides, proteins, and lipoproteins, which function as a matrix, holding biofilm cells together and protecting cells from antibiotics. By forming a matrix-encased multicellular aggregate, cells can also escape engulfment by phagocytic cells within a mammalian host. Extracellular polymeric substances not only promote bacteria to attach all kinds of surfaces (for example, a biomedical material or a mucosal surface of a biological organism), but also trap antibiotics or influence antibiotics to penetrate into the bacterial communities. Therefore, most drugs may only kill microorganisms on outer layer of the biofilm, yet microorganisms inside the biofilm may be the main reason for the generation of antibiotic-resistant mutation. Thus the biofilm may become a potential source of infections, which may cause refractory infections relating to clinical biofilms.

*Pseudomonas aeruginosa* (PA) is an environmental bacterium, and it is also an important human pathogen that may cause life-threatening persistent infections in humans, especially for burned patients and immune-compromised patients, and is the common pathogen in hospital-acquired infections. The persistence of *Pseudomonas aeruginosa* during these infections has been linked to its ability to form biofilms. Clinically, *Pseudomonas aeruginosa* may cause infections of blood, ears, eyes, skin and soft tissue, bone and joints, endocardium, respiratory system, etc. It is also the primary pathogen for causing pneumonia. Due to the intrinsic resistance of *Pseudomonas aeruginosa* to antibiotics and its biofilm formation ability, *Pseudomonas aeruginosa* infections are difficult to eradicate.

Therefore, there is an urgent need in the art for developing a preparation and a method for effectively inhibiting or disrupting a biofilm of a microorganism such as *Pseudomonas aeruginosa*.

SUMMARY

An object of the present disclosure is to provide a preparation and corresponding methods for effectively inhibiting or disrupting a biofilm of a microorganism such as *Pseudomonas aeruginosa*.

According to a first aspect of the present disclosure, the use of a PsIG protein or a nucleic acid encoding the PsIG protein is (i) for making a preparation for inhibiting, disrupting or disassembling a biofilm; and/or (ii) for making an antimicrobial agent.

In some embodiments, the biofilm may include a biofilm of *Pseudomonas*.

In some embodiments, the biofilm may be a biofilm of *Pseudomonas aeruginosa*.

In some embodiments, the PsIG protein may be a recombinant protein.

In some embodiments, the PsIG protein may be an isolated purified recombinant protein.

In some embodiments, the PsIG protein may be a mature form of a PsIG protein.

In some embodiments, the preparation may be selected from the following: a biofilm scavenger, a medical catheter cleaner, a medical cannula cleaner, a medical instrument pipe cleaner, a medical appliance disinfectant, an artificial joint cleaner, a bacteriostatic agent, a bactericide, a medical catheter care agent, a medical instrument care agent, or the like, or any combination thereof.

In some embodiments, the preparation may include a microbial film inhibitor.

In some embodiments, the preparation may include a catheter bacteria biofilm inhibitor, a biofilm inhibitor of a microorganism related to opportunistic infection.

In some embodiments, the biofilm may be in one or more articles selected from the following: a medical instrument, a catheter, or a medical appliance, or the like, or any combination thereof.

In some embodiments, the PsIG protein may be selected from: (i) a protein having an amino acid sequence of SEQ ID NO.: 2; (ii) a protein derived from (i), with one or more amino acid residues being substituted in, deleted from, and/or added into SEQ ID NO.: 2, wherein the derived protein may be capable of inhibiting formation of biofilm or degrading biofilm; and (iii) a protein that has at least 95% (preferably 98%) amino acid sequence identity to SEQ ID NO.: 2, wherein the protein may enhance its ability of biofilm inhibition or biofilm disruption.

In some embodiments, the encoding sequence of the PsIG protein may be selected from: (a) a nucleic acid that encodes a protein having the amino acid sequence of SEQ ID NO.: 2; (b) a nucleic acid having a nucleotide sequence of SEQ ID NO.: 1; (c) a nucleic acid having at least 95% (preferably 98%) nucleotide sequence identity to SEQ ID NO.: 1; (d) a nucleic acid having a nucleotide sequence which results from: 1-60 (preferably 1-30, more preferably 1-10) nucleotides being truncated from or added to the 5 end or 3 end of the nucleotide sequence of SEQ ID NO.: 1; (e) a nucleic acid having a nucleotide sequence complementary to the nucleotide sequence in any one of (a) to (d).

In some embodiments, the encoding sequence may encode the above PsIG protein selected from (i), (ii), or (iii).

In some embodiments, the PsIG protein or the encoding sequence thereof may be derived from *Pseudomonas aeruginosa*.

In some embodiments, the PsIG protein may be produced by recombinant cells.

In some embodiments, the recombinant cells may include prokaryotic cells (for example, *E. coli*) or eucaryotic cells.

In some embodiments, the recombinant cells may be selected from: *Pseudomonas aeruginosa, Pseudomonas stutzeri, Pseudomonas fluorescens (P. fluorescens)*, and *Pseudomonas syringae*.

In some embodiments, the preparation or the antimicrobial agent may be used for one or more uses of the following: (1) inhibiting formation of the biofilm of *Pseudomonas;* (2) disrupting and/or degrading formed biofilm of the *Pseudomonas;* and (3) inhibiting growth of the *Pseudomonas*.

In some embodiments, the *Pseudomonas* may be a *Pseudomonas* microorganism.

In some embodiments, the *Pseudomonas* may be selected from: *Pseudomonas aeruginosa, Pseudomonas stutzeri, Pseudomonas fluorescens, Pseudomonas syringae,* or the like, or any combination thereof.

In some embodiments, the *Pseudomonas* may be *Pseudomonas aeruginosa*.

In some embodiments, the preparation or pharmaceutical may be administered to a wound or wound surface of human or animal.

In some embodiments, the application may be body surface application.

In some embodiments, the concentration for application may be from 5 to 100 nM, and preferably from 10 to 50 nM; alternatively, the dose for application may be from 0.0001 to 10 g, and preferably from 0.001 to 1 g.

In some embodiments, modes of application may include: smearing, coating, spraying a wound, wrapping the wound with a wrapping material containing an effective concentration or amount of PsIG.

In some embodiments, the wound or wound surface may be caused by burns, trauma, surgery, intubation, or the like, and particularly suitable for wound surface and wound that are susceptible to microorganisms (particularly *Pseudomonas,* more particularly *Pseudomonas aeruginosa*) and/or easy to form a biofilm (particularly *Pseudomonas,* more particularly *Pseudomonas aeruginosa* biofilm) in either surface or inside thereof.

In some embodiments, dosage forms of the preparation or pharmaceutical may be solid dosage forms, liquid dosage forms or semi-solid dosage forms.

In some embodiments, dosage forms of the preparation or pharmaceutical may be selected from: lotions, powders, creams, tablets, coatings, film-forming adhesives, or the like, or any combination thereof.

In some embodiments, the preparation or pharmaceutical may be liquid.

In some embodiments, the preparation or pharmaceutical may be a powder form.

In some embodiments, the preparation or pharmaceutical may also contain an antibiotic.

In some embodiments, the antibiotic may be selected from: azithromycin, flaxacin (FLX), ciprofloxacin (CIP), tobramycin (TOB), or the like, or any combination thereof.

In some embodiments, the preparation may be an external preparation, and may also contain one or more optional ingredients selected from: a surfactant, a fragrances and a disinfectant.

According to a second aspect of the present disclosure, a biofilm inhibitor comprises (a) an effective amount of a PsIG protein, an active fragment thereof, and/or an agonist thereof; (b) a carrier; and (c) an optional adjuvant.

In some embodiments, the carrier may be a solvent (for example, water).

In some embodiments, the carrier may include a pharmaceutically acceptable carrier.

In some embodiments, the adjuvant may be selected from the following: a surfactant, a buffer, a pH regulator, or the like, or any combination thereof.

In some embodiments, the inhibitor may also include an antibiotic.

In some embodiments, the antibiotic may be selected from the following: azithromycin, flaxacin, ciprofloxacin, tobramycin, or a combination thereof.

In some embodiments, the inhibitor may be used for inhibiting a biofilm of *Pseudomonas*.

In some embodiments, the inhibitor may be used for treatment or adjuvant treatment of a disease relating to *Pseudomonas* infections.

In some embodiments, the inhibitor may be used for non-therapeutic killing or adjuvant killing of *Pseudomonas* in the environment.

According to a third aspect of the present disclosure, a pharmaceutical composition for inhibiting a biofilm may comprise: (a) a safe and effective amount of a PsIG protein, an active fragment thereof, and/or an agonist thereof; and (b) a pharmaceutically acceptable carrier.

In some embodiments, in the pharmaceutical composition, the content of the PsIG protein or the active fragment thereof may be in an amount from 0.0001 to 99% by weight, preferably from 0.001 to 90% by weight, more preferably from 0.01 to 50% by weight, based on the total weight of the composition.

In some embodiments, the pharmaceutical composition may also include an antibiotic.

In some embodiments, the antibiotic may be selected from the following: azithromycin, flaxacin, ciprofloxacin, tobramycin, or the like, or any combination thereof.

In some embodiments, the pharmaceutical may be used for inhibiting a biofilm of *Pseudomonas*.

In some embodiments, the pharmaceutical may be used for treatment or adjuvant treatment of a disease relating to a *Pseudomonas* infection.

According to a fourth aspect of the present disclosure, a non-therapeutic method of inhibiting and/or disrupting a biofilm in vitro, the method may comprise: apply a PsIG protein or the biofilm inhibitor according to the second aspect of the present disclosure to inhibit and/or disrupt the biofilm when needed.

In some embodiments, the concentration for application may vary from 5 to 100 nM, and preferably from 10 to 50 nM.

In some embodiments, the dose for application may vary from 0.0001 to log per square meter, and preferably from 0.001 to 1 g per square meter.

In some embodiments, the biofilm may be a biofilm of a *Pseudomonas species*.

In some embodiments, the biofilm may be a biofilm of *Pseudomonas aeruginosa*.

In some embodiments, the inhibitor ay contain water and/or an aqueous solvent.

According to a fifth aspect of the present disclosure, a method of altering biofilm formation capability in a bacterial strain of *Pseudomonas* may comprise:

(a) providing an original strain of the *Pseudomonas;*
(b) transforming the original strain with an encoding sequence of an exogenous a PsIG protein to produce a recombinant strain that contains the encoding sequence of the PsIG protein; and
(c) measuring the capability of the recombinant strain in forming biofilm and/or in producing the PsIG protein to select a recombinant strain that has a lower biofilm formation capability than that of the original strain or a higher capability in producing the PsIG protein than that of the original strain.

In some embodiments, the "higher than" may mean that the expression amount of the PsIG protein of the transformed recombinant strain is more than 1.5 times (≥) of that of the original strain before the transformation, and preferably more than twice times.

In some embodiments, the "lower than" may mean that the production amount of the transformed recombinant strain is lower than ½ (≤) of that of the original strain before the transformation, and preferably lower than ⅓.

According to a six aspect of the present disclosure, a preparation that is used to inhibit or disrupt a biofilm, the preparation may contain (a) a medically acceptable substrate, and (b) a PsIG protein that is coated or attached to the substrate.

In some embodiments, the preparation may include a preparation for wrapping a wound.

In some embodiments, the wound may include a wound surface and/or wound caused by burns, trauma, intubation, or the like, or any combination thereof.

In some embodiments, the preparation may include a preparation for human or veterinary use.

In some embodiments, the preparation ay also include (c) an antibiotic that is coated and attached to the substrate.

In some embodiments, the antibiotic may be selected from the following: azithromycin, flaxacin, ciprofloxacin, tobramycin, or the like, or any combination thereof.

In some embodiments, in the pharmaceutical composition, the content of the antibiotic may be in an amount from 0.0001 to 10% by weight, preferably from 0.001 to 5% by weight, more preferably from 0.01 to 2% by weight, based on the total weight of the preparation.

In some embodiments, the weight ratio of the PsIG protein to the antibiotic may vary from 1:1000 to 1000:1, preferably from 1:100 to 100:1; more preferably from 1:10 to 10:1.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

BRIEF DESCRIPTION OF THE DRAWINGS

FIG. 8(a) and FIG. 8(c) show results of MIC value measurement of TOB and CIP by a planktonic bacteria fluid; FIG. 8(b) and FIG. 8(d) show results of the MIC measurement of TOB and CIP by bacterial cells dispersed from a biofilm after PsIG treatment.

* FIG. 9(a) shows comparison of effects of PsIG and TOB with TOB alone; FIG. 9(b) show comparison of effects of PsIG and CIP with CIP alone.

FIG. 10 illustrates that PsIG has no cytotoxic effect on both colon epithelial cells and macrophages.

The PAO1 biofilm cultured on glass coverslips for 24 hours was treated with PsIG and co-incubated with macrophages, and then scraped and resuspended in 1 ml of physiological saline to quantify colony formation unit (CFU). The mean and SD values of CFU obtained by three repeated experiments were shown in the figure and T test (*, $P<0.01$) was performed for different experimental groups.

Figure 12:
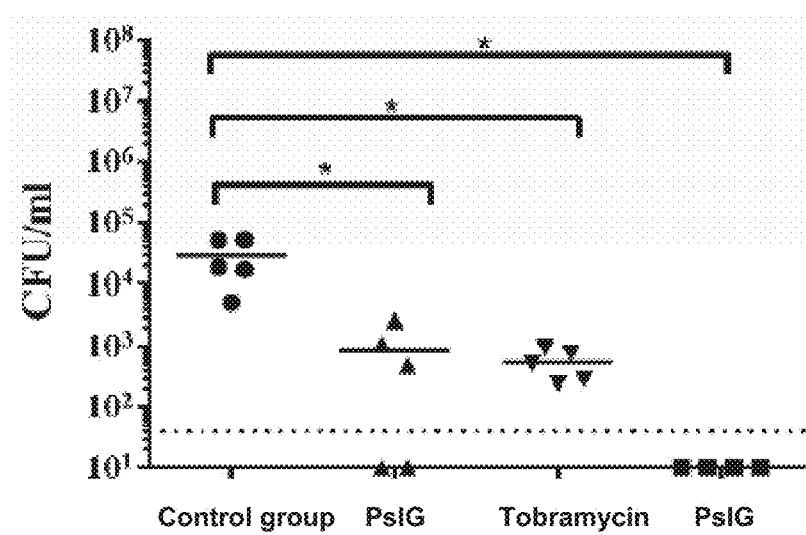

FIG. 12 illustrates a mouse implant infections model. PsIG improves host clearance of implant biofilms and show combinatory effect with Tob in eradication of implant biofilms in vivo. The horizontal dashed line represents a detection limit of the experiment, which is shown as mean (*$P<0.01$) of the biofilm counts in five mice.

Figure 13:
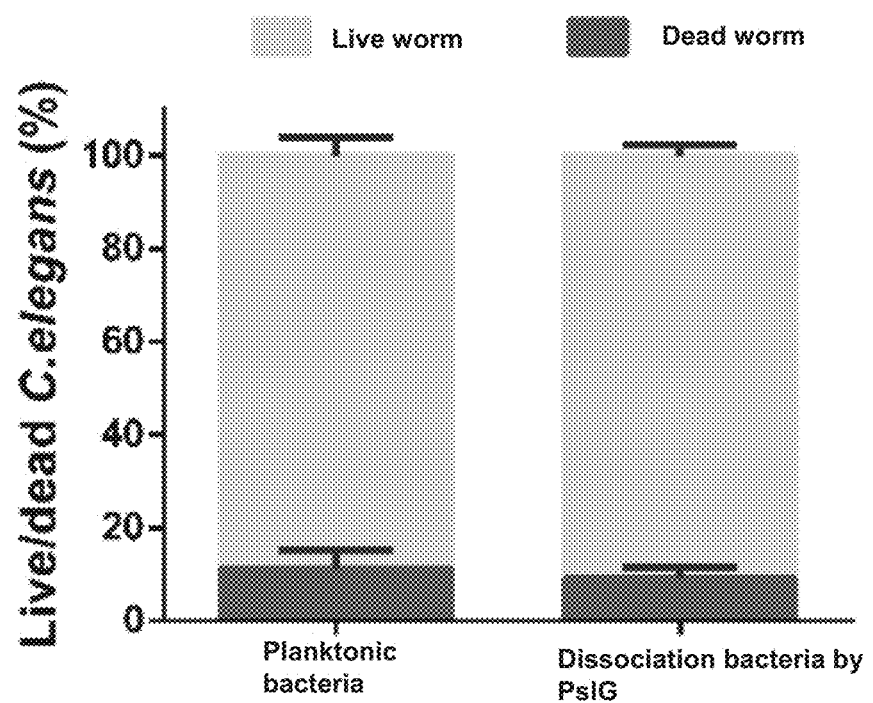

FIG. 13 illustrates the ratio of live nematodes and dead nematodes after the same amount of planktonic bacterial cells and bacteria dispersed from a biofilm by PsIG were incubated with L4-stage *Caenorhabditis elegans* respectively. The figure expresses the experiments result with a format of the mean value±SD value, and the experiments are repeated for three times.

Figure 14:
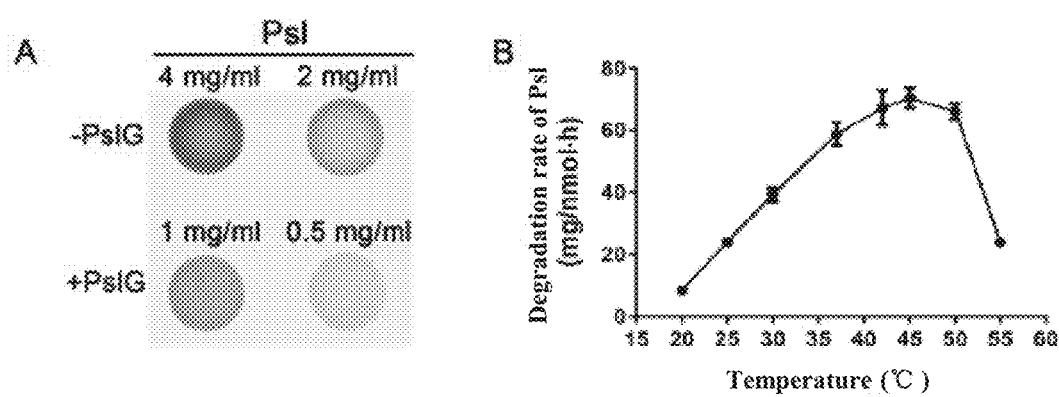

FIG. 14 illustrates degradation of the PsI polysaccharide by PsIG in vitro and degradation rate of the PsI polysaccharide by the PsIG protein at different temperatures. FIG. 14A illustrate results of dot immuno-blotting of the 4 mg/ml and 2 mg/ml of PsI polysaccharide before and after co-incubation with 50 nM PsIG for 1 h at 30 degrees centigrade, and the PsI polysaccharide concentration is marked above corresponding points after corresponding trace calculation; FIG. 14B illustrate the efficiency of degradation of PsI polysaccharide by the 50 nM PsIG protein at different temperatures. The experiment has been repeated for three times.

DETAILED DESCRIPTION

According to the research of the inventor, a protein (i.e., PsIG protein) from *Pseudomonas* species may effectively inhibit and disrupt a biofilm of a microorganism such as *Pseudomonas aeruginosa*. The present disclosure is accomplished based on this discovery.

Specifically, in some embodiments, the PsIG protein from *Pseudomonas aeruginosa* PAO1 effectively inhibits biofilm formation of *Pseudomonas aeruginosa*. The endogenous PsIG or PsIG supplied exogenously is capable of inhibiting biofilm formation of *Pseudomonas* species. Supplement of exogenous PsIG can disrupt a formed biofilm of *Pseudomonas aeruginosa*. After treatment with a biofilm inhibitor of the present disclosure, biomass of the biofilm has been reduced by at least 50%, and up to 80% under optimal conditions.

The present disclosure disclosed a three-dimensional crystal structure of the PsIG protein, and have revealed active sites of the PsIG protein relating to a disrupting function of the biofilm, and also preliminarily have revealed that the PsIG protein may degrade a purified extracellular polysaccharide PsI, which has indicated that the PsIG protein degrades extracellular polysaccharides to inhibit and disrupt the biofilm.

In some embodiments, using of the PsIG protein in combination with an antibiotic may have significantly better synergistic bactericidal effects than using the antibiotic alone.

*Pseudomonas* and *Pseudomonas Aeruginosa*

*Pseudomonas aeruginosa* (PA) is one of *Pseudomonas* species, which is an opportunistic pathogen that can cause infections in individuals with a compromised immune system, and patients with burned wound. It is also a common pathogen in hospital-acquired infections. The Infections caused by *Pseudomonas aeruginosa* is difficult to be eradicated due its biofilm formation ability.

*Pseudomonas aeruginosa* depend on extracellular polysaccharides, extracellular proteins, and extracellular DNA to maintain a biofilm structure thereof. Therefore, enzymes or factors that disrupt the components of biofilm matrix may disassemble or disperse biofilm, rendering biofilm bacteria sensitive to antibiotics and phagocytic cells.

In some embodiments, a specific PsIG protein has been used to degrade an extracellular polysaccharide PsI, which plays a key role in formation of a biofilm of *Pseudomonas*, thereby inhibiting and disrupting the biofilm of *Pseudomonas*.

Biofilm

In the present disclosure, "Biofilm" generally refers to surface-attached communities of microorganism encased by extracellular polymeric substances, and is prevalent in natural environment.

Biofilms enhance survival, enabling organisms to adapt to changing conditions collectively instead of as single cells. Hence biofilm formation thereof may bring serious harm to human. For example, in medicine, researches have indicated that about 65% human bacterial infections are relating to the biofilm, and resistance of the microorganisms to antibiotics in the biofilm is hundreds or even thousands of times higher than that in the planktonic state, which greatly increases difficulties for clinical treatment. For another example, in industry, the biofilm may contaminate water supply and drainage piping systems, and may cause a series of industrial problems relating to biofouling, such as biofilms on inner walls of pipes may cause water contamination, corrosion effects of the biofilms may shorten service life of piping facilities.

Medically, the biofilm may be a structured microbial cell population enmeshed within a protective extracellular matrix consisting of extracellular polysaccharide (also called exopolysaccharide), proteins, and DNA. Microbial communities may be attached to a surface of an active film and live animal and plant cells, and may be a sessile population.

PsIG Protein and Gene for Encoding PsIG

In the present disclosure, terms "protein of the present disclosure", "PsIG protein", "PsIG polypeptide", "PsIG enzyme" may be used interchangeably, and may be derived from a protein with unknown functions encoded by *Pseudomonas aeruginosa* a PsIG gene or other similar microorganism homologous protein. It should be understood that the terms may also include a wild type and a mutant type of the PsIG protein, including a full-length form of the PsIG protein (for example, from position 1 to position 442 of SEQ ID NO.: 2) or a mature form (for example, from position 31 to position 442 of SEQ ID NO.: 2), and an active fragment or a derived protein of the PsIG protein. In the present disclosure, a wild type, a mutant type or a mature form of these proteins, or the active fragment thereof or the derived protein thereof may reserve a function of inhibiting and/or disrupting a biofilm (particularly, a biofilm of *Pseudomonas*). In addition, it should be understood that the terms may include not only proteins derived from *Pseudomonas aeruginosa* but also homologous proteins from *Pseudomonas* or other microorganisms (typically, these homologous proteins from other species having at least about 60% amino acid sequence identity to SEQ ID NO.: 2, more preferably 70%, 80%, 90%, and most preferably 95%). In addition, it should be understood that the terms may include a protein form with or without a starting amino acid (Met).

In some embodiments, the nucleotide sequence of the full-length PsIG is shown in SEQ ID NO: 1, while the sequence of PsIG cloned into *E. coli* expression vector is starting from the 91st nucleotide of the full-length PsIG The amino acid sequence of a purified PsIG protein (31-442) may be shown in SEQ ID NO.: 2. In some embodiments, the PsIG protein may be derived from a *P. aeruginosa* PAO1 strain of *Pseudomonas aeruginosa*, which contains 442 amino acids in full length and contains a signal peptide (position 1 to position 30). A mature form of PsIG after removal of signal peptides (1-30) may have 411 amino acids in length.

Whether the amino acid sequence of PsIG is a full-length form or a mature form, the amino acid sequence of PsIG may perform expression and purification by conventional methods. A common expression system may perform expression by using *E. coli*.

The present disclosure has indicated that the PsIG may not only be capable of disrupting a biofilm produced by *Pseudomonas*, but also be capable of inhibiting formation of the biofilm of *Pseudomonas*.

The present disclosure reveals that the PsIG may have inhibitory and disruption effects on the biofilm of *Pseudomonas* for the first time.

Biofilm Inhibitor

In the present disclosure, "microbial community inhibitor" and "biofilm inhibitor" may be used interchangeably, and may generally inhibit communication or interconnection between microorganisms to inhibit a biofilm structure, but may not kill the microorganisms, hence do not produce stress on survival of the microorganisms, and thus do not lead to new "resistance".

In the present disclosure, terms "biofilm inhibitor of the present disclosure", "preparation of the present disclosure" may be used interchangeably, and all may refer to contain a PsIG protein, an active fragment thereof and/or an agonist thereof as an active ingredient so as to inhibit, disrupt or degrade a composition or a mixture of the biofilm of *Pseudomonas*.

In the present disclosure, there has been provided a biofilm inhibitor (also referred to as a biofilm disrupting agent) that contains the protein of the present disclosure as an active ingredient for inhibiting and/or disrupting a biofilm.

The biofilm inhibitor of the present disclosure may include:
(a) a PsIG protein, an active fragment thereof, and/or an agonist thereof; and
(b) a carrier and/or an adjuvant.

The biofilm inhibitor of the present disclosure may inhibit the biofilm of the microorganism and cause a pathogenic microorganism to loss protection and increase susceptibility to common pharmaceuticals, thereby achieving effective control of a plurality of pathogens, so that the biofilm inhibitor has an incomparable technical advantage with respect to ordinary antibiotic means.

In addition, the biofilm inhibition of the present disclosure may also be in combination with other substances (such as, antibiotics) selected from the following. Representative examples of antibiotics may comprise azithromycin, flaxacin, ciprofloxacin, tobramycin, or the like, or any combination thereof.

In some embodiments, the PsIG protein used in combination with antibiotics may have a significantly better synergistic bactericidal effect than antibiotics alone, The biofilm inhibitor of the present disclosure may effectively and/or specifically inhibit a microbial biofilm, and representative microorganisms may include microorganisms of *Pseudomonas*, particularly, *Pseudomonas aeruginosa*, *Pseudomonas stutzeri*, *Pseudomonas fluorescens*, and *Pseudomonas syringae*, or the like, or any combination thereof.

In some embodiments, the biofilm inhibitor may be used for different applications and situation. Representative examples include, but are not limited to, clearance and cleaning of biofilms of medical equipment and means pipes, clearance of catheter biofilm, inhibition of microbial films of medical catheters and other pipes.

In the present disclosure, an effective concentration for application or dose of the protein or the biofilm inhibitor may be not particularly limited and may be determined depending on the bacteria species, application occasions, or the like, or any combination thereof. The concentration for application may be preferably vary from 5 to 100 nM, and more preferably from 10 to 50 nM; or the dose for application may be from 0.0001 to 10 g, and preferably from 0.001 to 1 g (for example, per one or ten square meters).

In some embodiments, the biofilm inhibitor of the present disclosure may inhibit, disrupt or degrade the biofilm of *Pseudomonas*.

Pharmaceutical Composition and Application Method

The present disclosure provides a pharmaceutical composition that contains (a) a safe and effective amount of a PsIG protein, an active fragment thereof, and/or an agonist thereof; and (b) a pharmaceutically acceptable carrier. The carrier may include, but not limited to, brine, buffers, glucose, water, glycerol, ethanol, or a combination thereof. The pharmaceutical preparation may match a mode of application. The pharmaceutical composition of the present disclosure may be prepared by injections or a powder, for example, by physiological saline or an aqueous solution containing glucose and other adjuvants by a conventional method or by lyophilization. The pharmaceutical composition such as tablets and capsules may be prepared by a conventional method. The pharmaceutical composition such as injections, powders, tablets and capsules may be suitably made under aseptic conditions. The application amount of the active ingredient is a therapeutically effective amount, such as about 1 microgram per kilogram of body weight per day to about 5 milligram per kilogram of body weight per day. In addition, the pharmaceutical composition of the present disclosure may also be used in combination with antibiotic.

When a pharmaceutical composition is used, a safe and effective amount of the PsIG protein of the present disclosure is applied to a mammal, the safe and effective amount may be usually at least about 10 microgram per kilogram of body weight and, in most cases, no more than about 8 milligram per kilogram of body weight, preferably, the dose is from about 10 microgram per kilogram of body weight to about 1 milligram per kilogram of body weight. Specific dose may also consider routes of application, health conditions of patients and other factors. For persons having ordinary skills in the art, a certain amount of variations, changes, and/or modifications may be deduced under the guidance of the present disclosure. Those variations, changes, and/or modifications do not depart from the scope of the present disclosure.

Methods of inhibiting and/or disrupting biofilm

The present disclosure also provides a method of applying a protein, a biofilm inhibitor or a pharmaceutical composition to inhibit, disrupt or degrade a biofilm.

In some embodiments, the biofilm inhibitor concentration may vary from 5 to 100 nM, and preferably from 10 to 50 nM. In some embodiments, the biofilm may include a bacterial biofilm or a microbial film.

In some embodiments, the biofilm may include a catheter bacterial biofilm and/or a biofilm of microorganism relating to an opportunistic infection.

In some embodiments, the biofilm may be a biofilm of *Pseudomonas*.

In some embodiments, the biofilm may be a biofilm of *Pseudomonas aeruginosa*.

The method of the present disclosure may be applied for medicine uses, such as prevention, treatment, and may also be applied for non-therapeutic medicine uses, such as adjuvant killing microorganisms in the environment. Representative application methods may include, but not limited to:
(1) treating different burn patients and immune-deficient patients that are infected by *Pseudomonas aeruginosa* from different ethnic groups, different age or different regions;
(2) clearance and cleaning of biofilms of medical equipment and means pipes, clearance of catheter biofilm, inhibition of microbial films of medical catheters and other pipes.

The present disclosure provides a use of a PsIG protein and corresponding encoded sequence thereof for inhibiting, disrupting or disassembling a biofilm of a microorganism. Main advantages of the present disclosure may include:
(a) The PsIG protein may have inhibitory and disruption effects on the biofilm of *Pseudomonas* for the first time.

The biofilm inhibitor may be capable of particularly inhibiting or disrupting the biofilm of *Pseudomonas aeruginosa;*

(b) The present disclosure has parsed a crystal structure of the PsIG protein, and has revealed functions of the PsIG protein, for the first time;

(c) The present disclosure has found two key active sites of the PsIG proteins;

(d) Compared with using antibiotics alone, the PsIG protein used in combination with antibiotics may not only inhibit formation of the biofilm of *Pseudomonas aeruginosa,* and may be expected to completely clear *Pseudomonas aeruginosa.*

Therefore, the present disclosure may have potentially broad application prospects, for example, that may be expected to be developed as an antimicrobial agent and eliminate the resistance of *Pseudomonas aeruginosa.*

The present disclosure is further described below with reference to specific examples. It should be understood that these examples are merely used for illustrating the present disclosure, but are not intended to limit the scope of the present disclosure. The experimental methods not described in detail in the following examples are generally carried out according to conventional conditions, such as those described in Sambrook et al., Molecular Cloning: Laboratory Manual (New York: Cold Spring Harbor Laboratory Press, 1989), or according to conditions proposed by manufacturers. Unless otherwise stated, percentages and parts are by weight.

The experimental materials used in examples of the present disclosure are commercially available from the commercially available channel, unless otherwise stated, *Pseudomonas aeruginosa* PAO1 may be found in the reference, for example, paper in *Nature* 2000, 406: 959-964, titled Complete genome sequence of *Pseudomonas aeruginosa* PAO1, an opportunistic pathogen, the contents of which are hereby incorporated by reference.

Jensen's medium may be found in the reference, for example, paper in Journal of Bacteriology 1980, 144:844-847, titled Nutritional factors controlling exocellular protease production by *Pseudomonas aeruginosa,* the contents of which are hereby incorporated by reference. The Jensen's medium may contain a solute and a solvent. The solvent is water, and the solute and a concentration thereof may be: NaCl 5 g/L, $K_2HPO_4$ 3.286 g/L, glutamic acid 15.56 g/L, valine 2.81 g/L, phenylalanine 1.32 g/L, glucose 12.81 g/L, $MgSO_4.7H_2O$ 0.33 g/L, $CaCl_2.2H_2O$ 0.021 g/L, $FeSO_4.7H_2O$ 0.0011 g/L, $ZnSO_4.7H_2O$ 0.0024 g/L.

EXAMPLE 1

Expression of PsIG in *Pseudomonas Aeruginosa* PAO1 Inhibits Biofilm Formation of PAO1 Strain

*Pseudomonas aeruginosa* with a PsIG that can be induced by arabinose-induced expression plasmid may be cultured in Jensen's liquid medium at 37 degrees centigrade overnight, and inoculated in Jensen's medium containing different concentrations of arabinose with 1% inoculum dose, respectively, and then cultured statically in a 96-well plate at 30 degrees centigrade for 24 hours. The PsIG may comprise a PsIG DNA, a PsIG RNA, a PsIG protein. The arabinose-induced expression plasmid may be a pHERD20T-PsIG. The pHERD20T-PsIG may be obtained by cloning PsIG to pHERD20T. The pHERD20T may be found in the reference, for example, Applied and Environmental Microbiology 2008, 74:7422-7426, the contents of which are hereby incorporated by reference.

The biomass of the biofilm has been detected by a crystal violet staining method. The method including: discarding cultures (bacteria that are not attached on wells.) in the wells, and washing three times. Then, the biofilm may be stained with 0.1% crystal violet, and washed three times, then the crystal violet combined in the biofilm may be dissolved with 30% acetic acid, and the value of OD560 thereof (for example, the concentration of the crystal violet) may be measured by a spectrophotometer to measure the biomass of the biofilm was measured. PAO1-derived PsI polysaccharide negative strain (PAO1, ΔpsI) may be used as a negative control, and PAO1-derived PsI polysaccharide inducible strain (PAO1, PBAD-psI) (arabinose used as an inducer) may be used as positive control.

Figure 1:
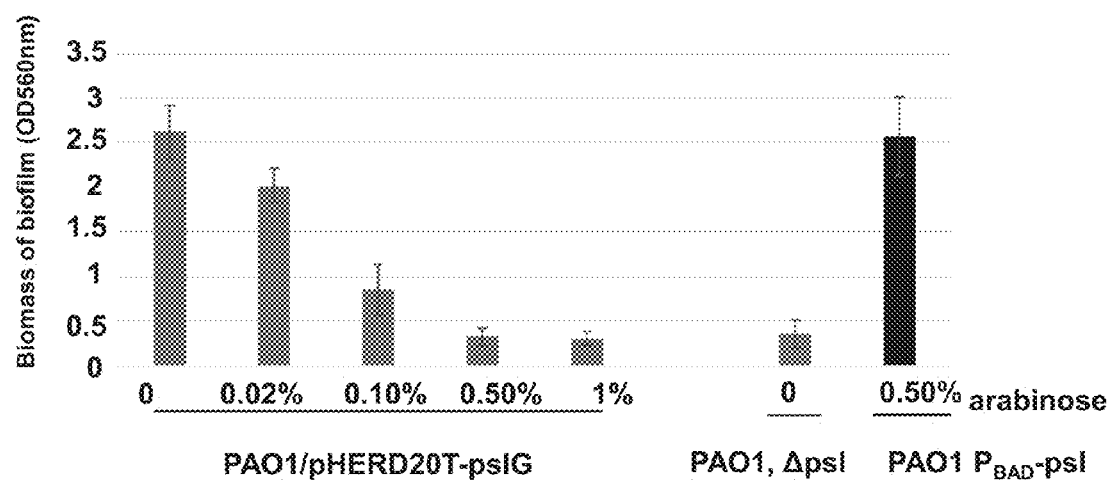
FIG. 1 illustrates that overexpression of a PsIG protein of a *Pseudomonas aeruginosa* PAO1 inhibits biofilm formation of the PAO1 strain.

As shown in FIG. 1, with the increase of the concentration of arabinose or the increase of PsIG expression, biomass of the biofilm of PAO1 may be gradually decreased. Not less than 0.5% of the concentration of arabinose may allow the biofilm of PAO1 reduce to the level of the ΔpsI strain.

The results have indicated that overexpression of the PsIG inhibited formation of the biofilm of the PAO1 strain.

EXAMPLE 2

Additional PsIG Exogenously Inhibits Formation of Biofilm of *Pseudomonas Aeruginosa*

A fresh single colony of *Pseudomonas aeruginosa* on the LBNS plate may be inoculated in LBNS liquid medium, carried out shake culture at 200 rpm at 37 degrees centigrade for 12 hours, and then inoculated in Jensen's medium with 1% inoculum dose, at the same time, different concentrations of PsIG protein may be added. After static culture in a 96-well plate at 30 degrees centigrade for 24 hours, liquid cultures were discarded and the biofilm may be stained with the crystal violet, and biomass of the biofilm was detected, in which specific operations may refer to the steps in Example 1.

Figure 2:
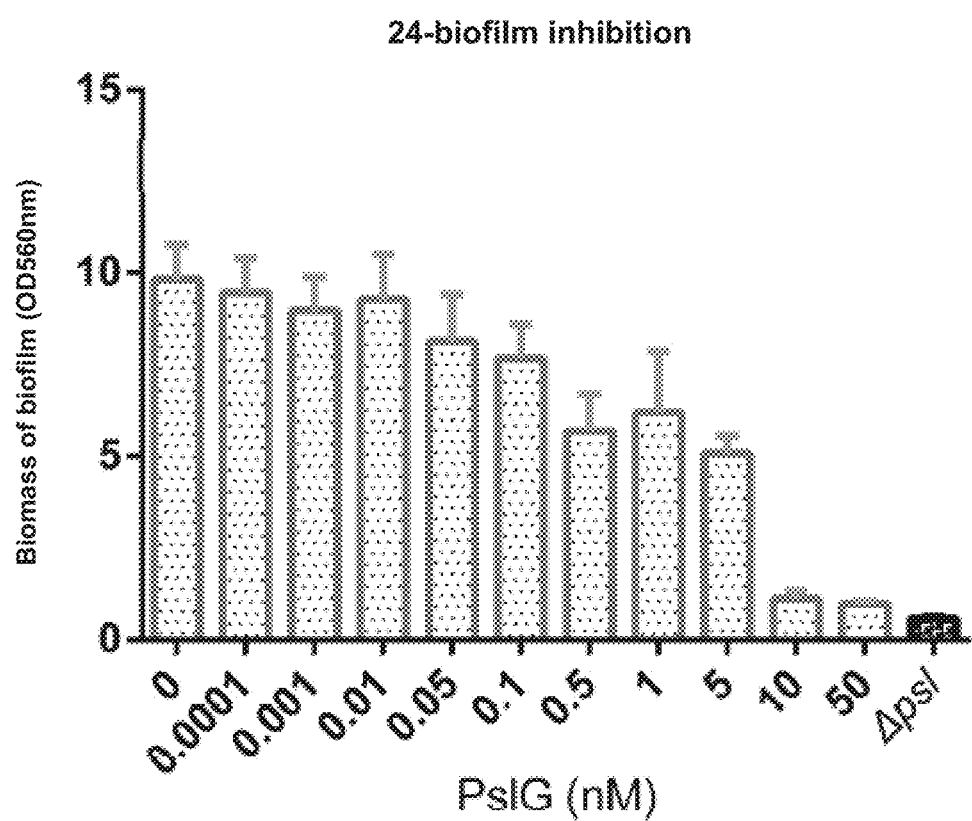
FIG. 2 illustrates that the addition of PsIG inhibits biofilm formation of *Pseudomonas aeruginosa;*

As shown in FIG. 2, an inhibitory rate of the PsIG protein at 1 nM may reach 50%. When the concentration is 10nm-50nm, the PsIG protein may significantly inhibit formation of the biofilm of *Pseudomonas aeruginosa.*

EXAMPLE 3

Disruption Effects of 1 nM PsIG on Formed Biofilm of *Pseudomonas Aeruginosa*

A fresh single colony of *Pseudomonas aeruginosa* on the LBNS plate may be inoculated in LBNS liquid medium, carried out shake culture at 200 rpm at 37 degrees centigrade for 12 hours, and then inoculated in Jensen's media with 1% inoculum dose, with static culture in a 96-well plate at 30 degrees centigrade for 24 hours. Cultures may be discarded and the biofilm (surface-attached bacteria) was washed with 0.8% physiological saline for three times. 100 µl Jensen's media containing 1 nM PsIG may be added into wells and the biofilm treated for 5 or 30 minutes. Then, biomass of the treated biofilm may be detected by the crystal violet staining method, in which specific operation steps of the crystal violet staining method may refer to Example 2.

At the same time, Jensen's media without addition of PsIG may be used as a control group.

Figure 3:
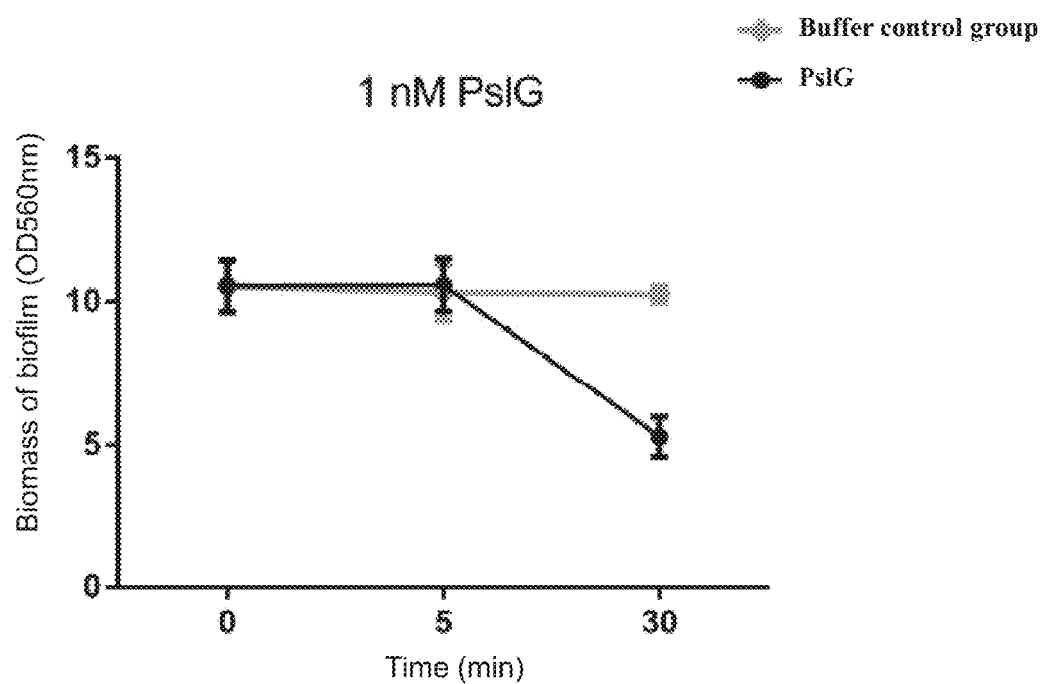
FIG. 3 illustrates that a 1 nM PsIG disrupts a formed biofilm of *Pseudomonas aeruginosa;*

As shown in FIG. 3, treatment by the 1 nM PsIG protein for five minutes may have no effect on biomass of the biofilm of *Pseudomonas aeruginosa*. But the biomass of the biofilm treated for 30 minutes may have reduced by 50%.

EXAMPLE 4

Disruption of Formed Biofilm of *Pseudomonas Aeruginosa* by 50 nM PsIG Protein

A fresh single colony of *Pseudomonas aeruginosa* on the LBNS plate may be inoculated in LBNS liquid medium, carried out shake culture at 200 rpm at 37 degrees centigrade for 12 hours, and then inoculated in Jensen's media with 1% inoculum dose, and carried out static culture in a 96-well plate at 30 degrees centigrade for 24 hours. Cultures were discarded and the biofilm was washed with 0.8% physiological saline for three times. 100 µl Jensen's media containing 50 nM PsIG protein was added and the biofilm was treated for different times. Then, biomass of the treated biofilms may be tested by a crystal violet staining method, in which specific operation steps of the crystal violet staining method may refer to Example 2.

At the same time, Jensen's media without addition of PsIG may be used as a control group.

Figure 4:
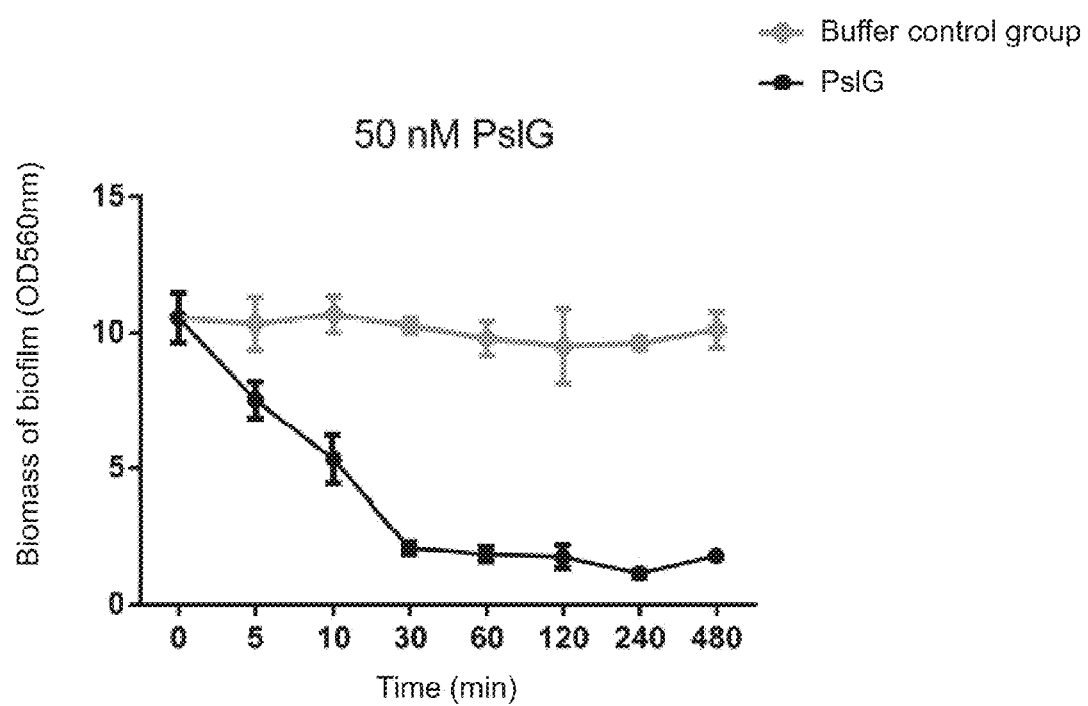
FIG. 4 illustrates that a 50 nM PsIG disrupts a formed biofilm of *Pseudomonas aeruginosa;*

As shown in FIG. 4, treatment by the 50 nM PsIG protein for five minutes has significantly reduced the biomass of the biofilm of *Pseudomonas aeruginosa*; and the biomass of the biofilm treated for 10 minutes has been reduced by 50%; the biomass of the biofilm treated for 30 minutes has been reduced to a level similar to the PsI polysaccharide-negative strain. But there is no more significant reduction by treatment for more than 30 minutes.

In some embodiments, the treatment with 50 nM PsIG for 30 minutes is sufficient to clear the biofilm that is dependent on PsI polysaccharide.

EXAMPLE 5

E156 and E276 are Key Active Sites of PsIG Protein

In some embodiments, E156 and E276 may be key catalytic sites thereof after repeated comparison and analysis. Crystal structure analysis of PsIG protein has shown that E156 and E276 may be key catalytic sites thereof.

Figure 5:
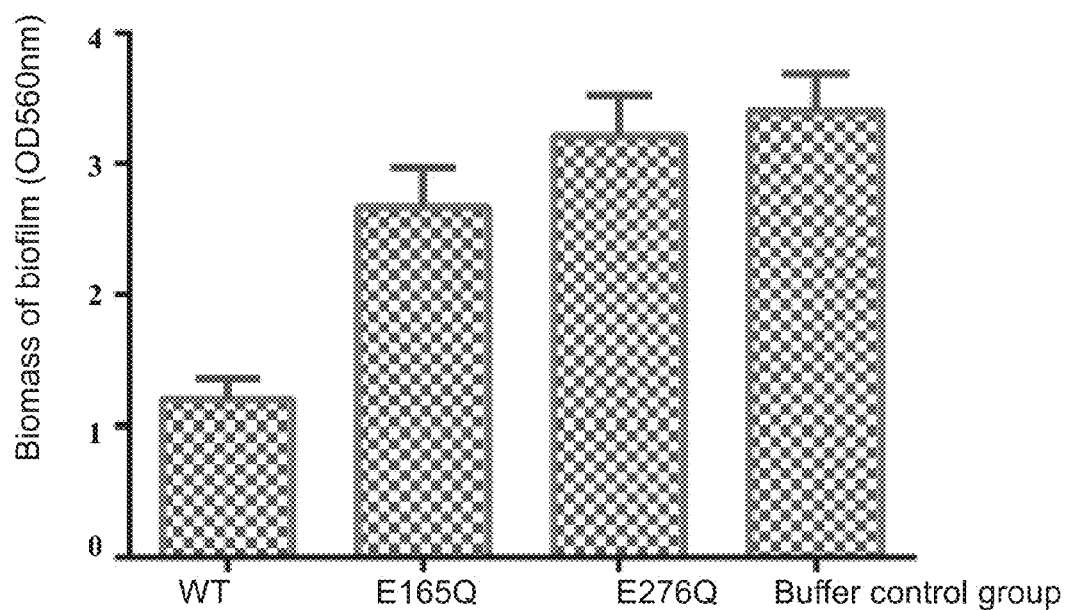
FIG. 5 illustrates a result of treatment of a 6-hour biofilm of *Pseudomonas aeruginosa* for 30 minutes by PsIG (WT) and mutant proteins thereof E156Q, E276Q, wherein, E156 and E276 are key active sites of PsIG.

As shown in FIG. 5, mutant proteins PsIG (E1560) and PsIG (E276Q) have lost capacity in disrupting a formed biofilm of *Pseudomonas aeruginosa*.

EXAMPLE 6

Inhibitory Effects of PsIG Protein on Biofilm of *Pseudomonas Syringae*

The method is similar to Example 2, but the PsIG concentration is 50 nM.

Figure 6:
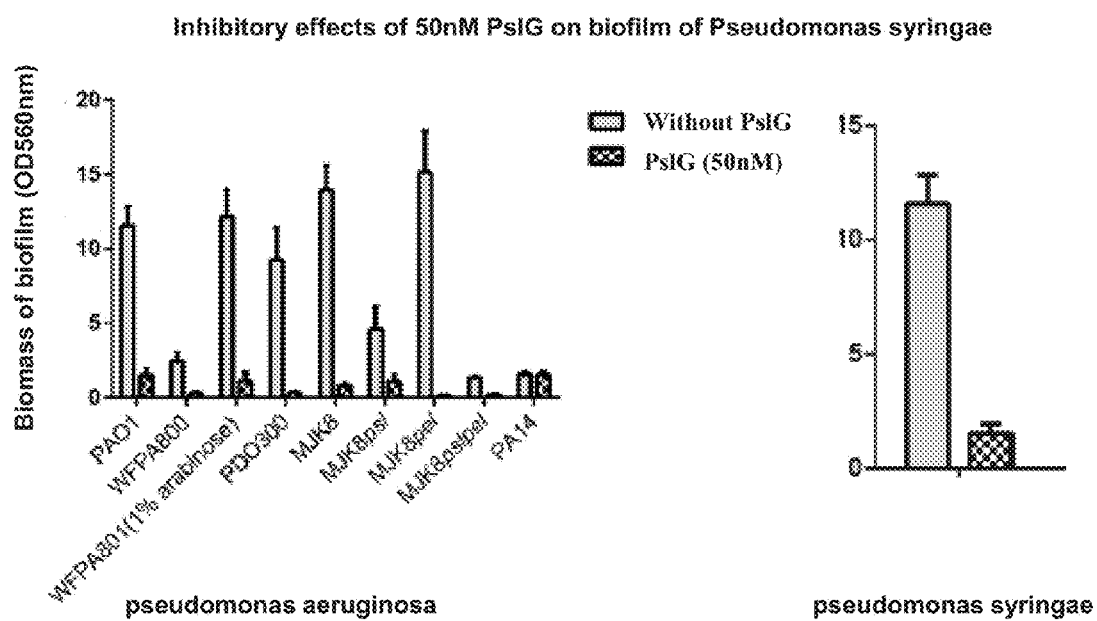
FIG. 6 illustrates inhibitory effects of a 50 nM PsIG on biofilms of *Pseudomonas syringae.*

As shown in FIG. 6, the results have indicated that the PsIG protein is capable of not only inhibiting the biofilm of *Pseudomonas aeruginosa* strains, but also having same inhibitory effects on *Pseudomonas syringae*.

EXAMPLE 7

Inhibitory Effects of Lyophilized PsIG Protein on Biofilm of *Pseudomonas Aeruginosa*

A powder may be obtained by freeze-drying the PsIG protein, and re-dissolved in sterile water. Then the biofilm inhibition experiment may be carried out, and the original PsIG protein solution without freeze-drying may be used as a control group. The method is similar to Example 2, but the PsIG protein concentration is 50 nM.

Figure 7:
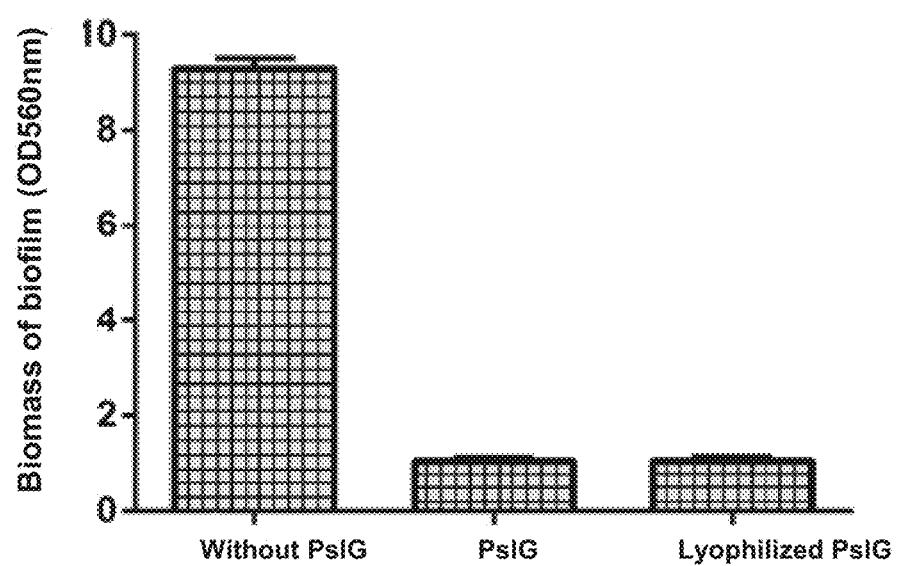
FIG. 7 illustrates biofilm inhibitory effects of PsIG with lyophilize.

As shown in FIG. 7, the results have suggested that both the lyophilized PsIG protein and the PsIG protein solution have similar inhibitory effects on the biofilm of *Pseudomonas aeruginosa*.

EXAMPLE 8

Comparison of Susceptibility to Antibiotics between PsIG-Treated Bacteria and Planktonic Bacteria The 24-hour old biofilm of *Pseudomonas aeruginosa* may be treated with a PsIG protein for 1 hours, and 0.2 ml of bacteria dispersed from a biofilm by PsIG was collected, then uniformly inoculated on the LBNS plates, and MIC test strips may be placed in the center of these plates, and MIC values may be read after incubation at 37 degrees centigrade for 16 hours. Planktonic *Pseudomonas aeruginosa* may be cultured for 24 hours with shocking in LBNS medium, and 0.2 ml of such culture may be used as control.

As shown in FIGS. 8(a) and 8(c), a control group have shown measurement of MIC values of TOB, CIP by a planktonic bacteria.

FIGS. 8(b) and 8(d) have shown measurement of MIC values of TOB, CIP by bacteria cells dispersed from the biofilm after the treatment of the PsIG protein.

Figure 8:
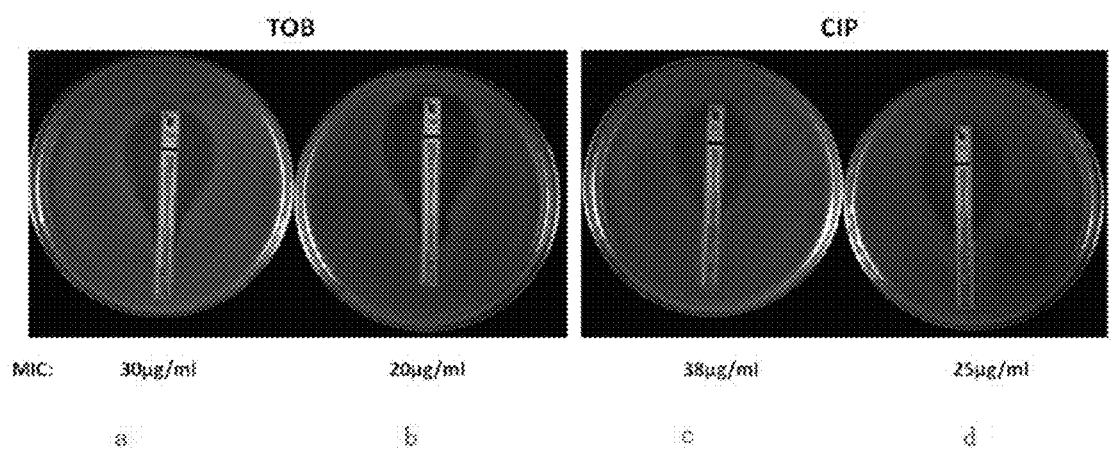
FIG. 8 illustrates comparison of effects on susceptibility to antibiotics between PsIG-treated bacteria and planktonic cells.

As shown in FIG. 8, the results have indicated that compared with planktonic cells, the bacteria dispersed from biofilms by PsIG may be more sensitive to tobramycin (TOB) and ciprofloxacin (CIP), and the MIC values thereof may be lower.

EXAMPLE 9

Figure 9:
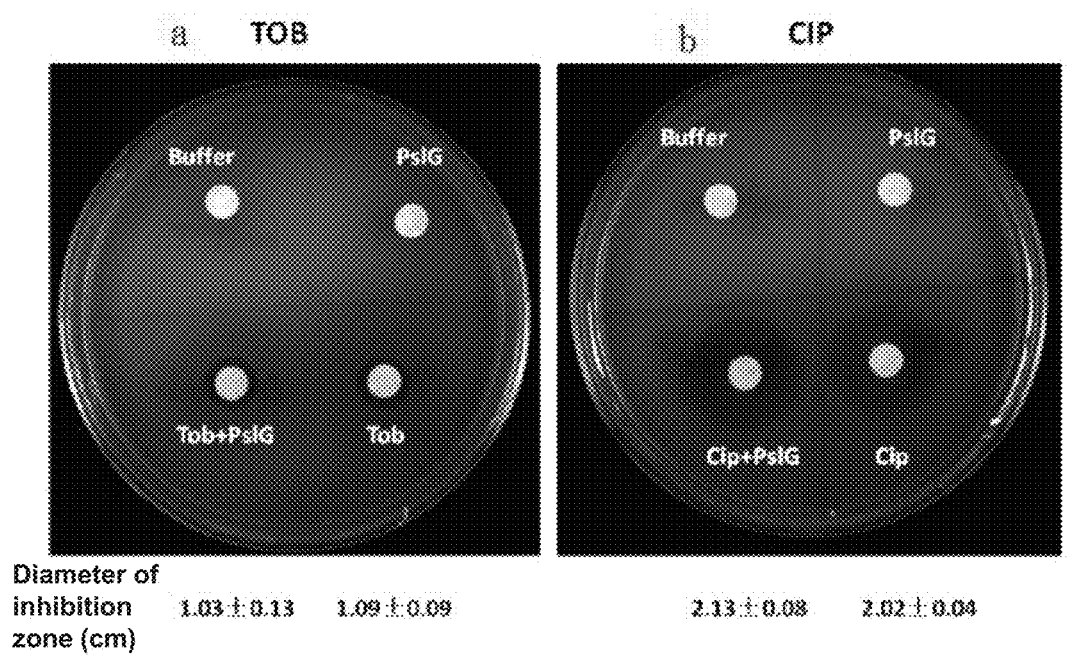
FIG. 9 illustrates effects of PsIG used in combination with antibiotics on *Pseudomonas aeruginosa.

PsIG Used in Combination with Antibiotics on *Pseudomonas Aeruginosa* May Not Affect Activity of Antibiotics The 0.2 ml of *Pseudomonas aeruginosa* culture after grown at 37 degrees centigrade for 24 hours may be inoculated on the LBNS plate, and filter paper with different antibiotics was placed on the plate, as shown in FIG. 9, inhibitory zone may be measured after incubation at 37 degrees centigrade for 24 hours. Experiment 1:

As shown in FIG. 9(a), four experimental groups may be set for buffer; 50 nM PsIG; tobramycin (TOB); combination of TOB and PsIG, respectively. Experiment 2:

As shown in FIG. 9(b), four experimental groups may be set for buffer; 50 nM PsIG; ciprofloxacin (CIP); combination of CIP and PsIG, respectively.

As shown in FIG. 9, there may have no significant change in diameter of the inhibitory zone by the PsIG protein used in combination with antibiotics compared with antibiotics alone. Therefore, the PsIG protein used in combination with antibiotics did not affect the activity of antibiotics; the PsIG protein alone does not produce inhibitory zone, which has indicated that the PsIG protein is no killing effect.

EXAMPLE 10

PsIG Used in Combination with Fleroxacin (FLX) Inhibits Formation of a Biofilm of *Pseudomonas Aeruginosa*

The minimum inhibitory concentration (MIC) of *Pseudomonas aeruginosa* to FLX may be measured according to a microdilution method (see Practical Clinical Bacteriology Test and Progress, 1993: 247 by Lou Yongxin, Wang Jinliang). The IC50 values of PsIG were measured by a conventional method.

PsIG protein of ½ IC50 may be respectively used in combination with a FLX of ¼ MIC and ½ MIC to measure inhibitory effects thereof on biofilms of *Pseudomonas aeruginosa*.

The results have indicated that bactericidal effects of PsIG used in combination with FLX on *Pseudomonas aeruginosa* may be more significant than that of 1MIC FLX alone.

EXAMPLE 11

PsIG has No Cytotoxic Effect on Mammal Epithelial Cells and Immunocytes

Cytotoxicity of a PsIG protein may be detected by human colon epithelial cell line Caco2 and HT-29.

Figure 10A:
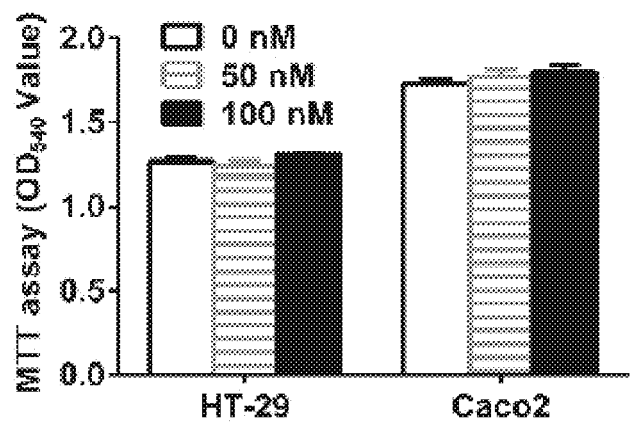
FIG. 10A illustrates that cytotoxicity of epithelial cells HT-29 and Caco2 was detected by MTT assay after a PsIG protein treatment for 12 hours.
Figure 10B:
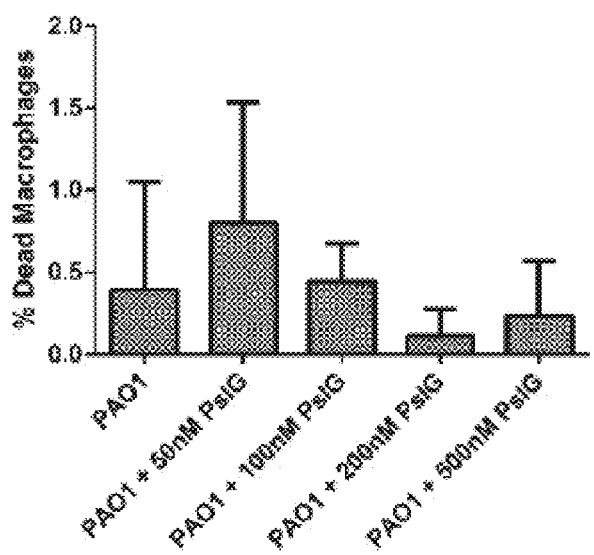
FIG. 10B illustrates that the PsIG protein has no cytotoxic effect on macrophages.

The results have shown in FIG. 10A and FIG. 10B, tetrazole MTT cytotoxicity test has shown that the PsIG protein has no effect on activity of two colon epithelial cells. Furthermore, the PsIG protein has not shown any toxic effects on mouse macrophages (RAW264.7).

EXAMPLE 12

PsIG-treated Biofilm Bacteria may be more Efficient for Clearance by Macrophages The PAO1 biofilm cultured on glass coverslips for 24-hours may be treated with the PsIG protein for 1 hour, and then incubated with macrophages for 2 hours, and remaining biofilm may be scraped and resuspended in 1 ml of physiological saline for colony formation unit (CFU).

Figure 11:
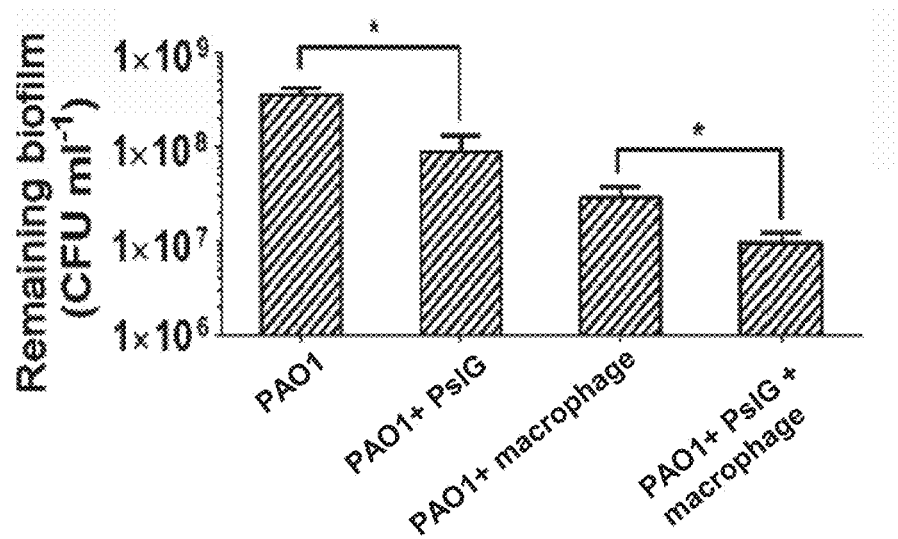
FIG. 11 illustrates that PsIG treatment sensitives biofilm bacteria to macrophages.

As shown in FIG. 11, compared to control groups without the PsIG protein treatment, the number of remaining bacteria of the biofilm treated by the PsIG protein and macrophages is least. The results have indicated that the PsIG protein may be capable of enhancing sensitivity of the biofilm to macrophage.

Therefore, the PsIG protein has no cytotoxicity to host cells and may enhance the sensitivity of the biofilm to macrophages, thereby suggesting potential application value of the PsIG protein in treatment of biofilm-related infections.

EXAMPLE 13

Mice Implanted Infection Model has Shown that PsIG could Promote Clearance of Biofilm in Vivo Implants coated by the biofilm of *Pseudomonas aeruginosa* may be inserted into mouse peritoneum and the following treatments may be performed locally: 50 nM PsIG treatment alone; 50 mg kg-1 tobramycin treatment alone; the 50 nM PsIG and the 50 mg kg-1 tobramycin co-treatment. After culture in vivo for 24 hours, mice may be sacrificed so as to harvest the implants, and the implants may be removed out and counted on LB plates after homogenization. The number of *Pseudomonas aeruginosa* on the implants may be tabulated with a format of CFU/ml.

As shown in FIG. 12, compared to the untreated control group, the number of bacteria on the implants treated with the PsIG protein or tobramycin alone or the PsIG protein and tobramycin may be significantly lower. Specifically, the number of bacteria in the control group (CFU/mL)>$10^4$, the number of bacteria treated with the PsIG protein alone(CFU/mL)≈$10^3$, the number of bacteria treated with tobramycin alone (CFU/mL)≈$10^{2.8}$, the number of bacteria after co-treatment with the PsIG protein and tobramycin (CFU/mL) has reached $10^1$. Therefore, the PsIG protein used in combination with tobramycin has the best effect.

The results have indicated that the PsIG protein and antibiotics may be used simultaneously to treat infections relating to clinical biofilms (such as a biofilm of *Pseudomonas aeruginosa*).

EXAMPLE 14

There was No Significant Change in Toxicity of Bacteria Dispersed from Biofilms by PsIG The experiment may be carried out by using *C. elegans* as a host model.

Two experimental groups may be set for Experimental group 1 and Experimental group 2, respectively.

Experiment group 1: the bacterial cells collected from a PsIG-treated bacterial biofilm (a biofilm of *Pseudomonas aeruginosa*) may be co-incubated with L4-stage *Caenorhabditis elegans*.

Experimental group 2: co-incubation the planktonic culture of *Pseudomonas aeruginosa* grown for 24 hours may be co-incubated L4-stage *Caenorhabditis elegans*.

Experimental group 1 and Experimental group 2 were placed in 96-well plates respectively and co-incubated at 25 degrees centigrade for 48 hours. The proportion of live and dead nematode was observed with a stereomicroscope. Each group was repeated for three times, the results are expressed with a format of the mean value±SD value.

As shown in FIG. 13, the results have indicated that there is no significant difference in toxicity between PsIG-dispersed biofilm bacteria (Experimental group 1) and planktonic bacteria (Experimental group 2).

EXAMPLE 15

Expression of PsIG Protein in *E. Coli*

A nucleotide sequence of SEQ ID NO.: 1 of a PsIG protein was inserted into a polyclone site of pET15b (available from Merck Millipore) to obtain a recombinant expression plasmid PGL01-psIG, a PsIG protein of SEQ ID NO.: 2 expressed by a PGL01-psIG. The expression plasmid PGL01-psIG may be transferred to *E. coli* BL21 (DE3) and cultured at 37 degrees centigrade to $OD_{600}$=0.8, and then induced at 22 degrees centigrade overnight after adding 0.12 thiogalactoside. Bacterial culture may be centrifuged at 4200 rpm for 15 minutes and resuspended in a binding buffer (25 mM Tris-HCl, pH 8.0, 200 mM NaCl). The bacteria in suspension may be broken by ultrasonic and centrifuged at 12000 rpm for 45 minutes to remove precipitation. A supernatant containing the PsIG protein may be passed through a nickel affinity column and may be washed with the binding buffer several times to remove non-specific binding proteins. The protein bound to the nickel column resin may be re-dissolved with the binding buffer mixed with phosphatase (0.12 mg/ml of final concentration). The mixture may be incubated at 4 degrees centigrade overnight to remove His tag and then the protein sample may be eluted with the binding buffer.

To further purify the protein, the PsIG protein passed an ion exchange column (Source 15Q HR 16/10, GE Healthcare) and eluted sequentially with 0-1 M NaCl in 25 mM Tris-HCl pH 8.0 buffer solution with linear concentration gradient. Finally, the protein sample with 10 mM Tris-HCl pH 8.0 buffer containing 100 mM NaCl passed a molecular sieve (Superdex 20010/300 GL, GE Healthcare) to obtain the PsIG protein with a molecular weight of 47 kDa.

EXAMPLE 16

The Degradation Effects of PsIG Protein on PsI Polysaccharide in Vitro and the Corresponding PsI-degradation Activity of PsIG Protein in Vitro at Different Temperatures Experiment Method:

Preparation and purification of PsI polysaccharide may be carried out with reference to published document (Molecular Microbiology 2009; 73:622-638, titled Genetic and biochemical analyses of the *Pseudomonas aeruginosa* PsI exopolysaccharide reveal overlapping roles for polysaccharide synthesis enzymes in PsI and LPS production, written by Byrd M S, Sadovskaya I, Vinogradov E et al.)

The standard curve may be prepared according to the following method: PsI polysaccharide prepared by the above method may be diluted 10 times with gradient and the PsI polysaccharide may be detected by immunoblotting.

To Solution 1 (PBS phosphate buffer), PsI polysaccharide and 50 nM of the PsIG protein obtained in Example 16 may be added to obtain Reaction system 1, the concentration of PsI polysaccharide in reaction system 1 may be 4 mg/ml, and the concentration of PsIG protein may be 50 nM. The eight same reaction systems 1 may be incubated at 20 degrees centigrade, 25 degrees centigrade, 30 degrees centigrade, 37 degrees centigrade, 40 degrees centigrade, 45 degrees centigrade, 50 degrees centigrade and 55 degrees centigrade for one hour, respectively, and then remaining PsI polysaccharide may be detected with a PsI polysaccharide antibody (the PsI polysaccharide antibody may be obtained by using PsI polysaccharide as immunogen) by immunoblotting. The signal intensity may be analyzed by the Quantity One (Bio-Rad) software and compared with the standard curve, to calculate a remaining amount of PsI polysaccharide at 4 mg/ml of an initial concentration of the PsI polysaccharide after PsIG protein treatment.

According to the above methods, the concentration of PsI polysaccharide may be changed from 4 mg/ml to 2 mg/ml, and the other steps may be unchanged, and the remaining amount of PsI polysaccharide at 2 mg/ml of an initial concentration of PsI polysaccharide after PsIG protein treatment may be obtained.

According to the above methods, the 50 nM PsIG protein may be replace with 0 nM PsIG protein, and the remaining amount of PsI polysaccharide at 4 mg/ml of an initial concentration of PsI polysaccharide without PsIG protein treatment is obtained.

According to the above method, the concentration of PsI polysaccharide may be changed from 4 mg/mi to 2 mg/ml, and 50 nM PsIG protein may be replaced with 0 nM PsIG protein to obtain a remaining amount of polysaccharide under 2 mg/ml of initial PsI concentration without PsIG protein treatment.

Experiment Result:

(1) Results of the PsI polysaccharide treated with the 50 nM PsIG protein and the 0 nM PsIG protein at 30 degrees centigrade for 1 hour are shown in FIG. 14A. The results have shown that the amount of the PsI polysaccharide with the PsIG protein treatment has been reduced by 75% compared with untreated control. The results have indicated that the exogenous PsIG protein may be capable of effectively degrading the PsI polysaccharide in vitro.

(2) Degradation rates of the PsI polysaccharide by the PsIG protein at different temperatures are shown in FIG. 14B. The results have indicated that the degradation rate by the PsIG protein may be the highest at 45 degrees centigrade, and there may be active at 20 to 55 degrees centigrade.

All documents mentioned in the present disclosure are incorporated herein by reference, as each document was individually recited for reference. It should be understood that those skilled in the art will be able to make various changes or modifications to the present disclosure after reading the teachings of the present disclosure, which also fall within the scope of the claims appended hereto.

We claim:

1. A method of inhibiting formation of biofilm on a surface, comprising contacting the surface with a composition comprising a PsIG protein and at least one antimicrobial agent, wherein the PsIG protein increases the activity of the antimicrobial agent to inhibit formation of the biofilm and consists of an amino acid sequence of SEQ ID NO: 2, wherein a concentration of the PsIG protein is in a range of 5 nM to 100 nM and has no cytotoxicity.

2. The method of claim 1, wherein the at least one antimicrobial agent is selected from the group consisting of azithromycin, fleroxacin, ciprofloxacin, and tobramycin.

3. The method of claim 1, wherein the at least one antimicrobial agent comprises fleroxacin.

4. The method of claim 1, wherein the composition further comprises a pharmaceutically/environmentally acceptable carrier.

5. The method of claim 1, wherein the composition is lyophilized.

6. The method of claim 1, wherein the PsIG protein has an in vitro activity of degrading 75% Psi polysaccharide at 30° C. in one hour.

7. The method of claim 1, wherein the biofilm is formed by *Pseudomonas* species or is contained *Pseudomonas* species.

8. The method of claim 1, wherein the biofilm is formed on a surface of a medical device or a surface of a pipe.

9. The method of claim 1, wherein the PsIG protein is at a concentration that has no cytotoxicity to Caco2, HT-29 cells, or nematodes.

10. A method of disrupting a biofilm, comprising contacting the biofilm with a composition comprising a PsIG protein, wherein the PsIG protein consists of an amino acid sequence of SEQ ID NO: 2, wherein a concentration of the PsIG is in a range of 5 nM to 100 nM and has no cytotoxicity.

11. The method of claim 10, further comprising contacting the biofilm with at least one antimicrobial agent.

12. The method of claim 11, wherein the at least one antimicrobial agent is selected from the group consisting of azithromycin, fleroxacin, ciprofloxacin, and tobramycin.

13. The method of claim 11, wherein the at least one antimicrobial agent comprises tobramycin.

14. The method of claim 10, wherein the composition further comprises at least one of a pharmaceutically acceptable carrier and an environmentally acceptable carrier.

15. The method of claim 10, wherein the composition is lyophilized.

16. The method of claim 10, wherein the PsIG protein has an in vitro activity of degrading 75% Psi polysaccharide at 30° C. in one hour.

17. The method of claim 10, wherein the biofilm is formed by *Pseudomonas* species or is contained *Pseudomonas* species.

18. The method of claim 10, wherein the biofilm is formed on a surface of a medical device or a surface of a pipe.

19. The method of claim 10, wherein the PsIG protein is at a concentration that has no cytotoxicity to Caco2, HT-29 cells, or nematodes.

* * * * *

SEQUENCE LISTING

```
<160> NUMBER OF SEQ ID NOS: 2

<210> SEQ ID NO 1
<211> LENGTH: 1329
<212> TYPE: DNA
<213> ORGANISM: Pseudomonas aeruginosa

<400> SEQUENCE: 1
atggcacgta  agggactcta  tctgggcggc  agcgcgctgc  tgctcgccgt  ggtactgctg      60
ctggtgttct  gggggcgtcc  cgccgacgcc  gagatccagg  tactgaaggc  gcctcgcgcg     120
gtggtctgga  aagacttcct  cggggtcaac  gcgcagttcc  tctggttcag  cccggagcgt     180
tacaacaagc  agatcgaccg  cctgcaggac  ctggggctgg  agtgggtgcg  cctggacctg     240
cactgggacc  gcctggaaac  cgccgaggac  cagtaccagc  tggcctccct  cgaccagttg     300
gtcaaagatc  tcgaggcgcg  ccagctgaag  tcggtgttct  acctggtcgg  ctcggcccgc     360
ttcatcacca  ccgcgccgtt  ctactcgccc  ttccaggacc  agtatccgcc  gcgcgacccg     420
gaagtcttcg  cccggcgcat  ggcgatgctc  tcgcagcgct  acccgagcgt  ggccgcctgg     480
caggtatgga  acgagcccaa  cctgatcggc  ttctggcggc  ccaaggccga  cccggaaggc     540
```

```
tacgccaagc tgctccaggc cagcaccatc gccctgcgca tggtcgaccc ggagaagccg      600
gtggtttccg ccggcatggc cttcttcagc gagatgcccg acggccgcac catgttcgac      660
gccctcggcc acctgggcgt ggagagcctc ggcaccatcg ccacctacca ccctatacc       720 cagttgccgg aaggcaacta cccgtggaac ctggacttcg tctcccacgc caaccagatc      780
aaccgcgccc tgcgcaacgc cggcgtgccg gcgatctgga caccgagtg gggctggtcg       840 gcctacaagg ggccgaagga gttgcaggac atcattggcg tcgaaggcca ggccgactac      900
gtgctgcgtc gcctggcgct gatgagtgcg ctggactacg accggatctt cctcttcacc      960
ctcagcgatc tcgaccagcg cgccagcgtg cgcgaccgcg actacggcct gctcgacctg     1020
gacgccaacc ccaagccggt ctacctggcc ctgcaacgct tcctcaaggt caccgggccg     1080
aagctgcgcc cggccgaccc gccggtcacc gaggacctgc ccgacggttc cttcagcatc     1140
ggctggaccc gcgaggacgg tcgcaacgtc tggctgttct ggtcggcccg cggcggcaac     1200
gtgcgcctgc cgaagctcaa ggaggccacc ctgcacgatc cgctcagcgg caaggtcacg     1260
cccttgagcg gcagcgacgg cctggaagtc ccggtgaagt ccagcctgca gatgctggtc     1320
tgggagtga                                                             1329
```

<210> SEQ ID NO 2
<211> LENGTH: 412
<212> TYPE: PRT
<213> ORGANISM: Pseudomonas aeruginosa

<400> SEQUENCE: 2

```
Glu Ile Gln Val Leu Lys Ala Pro Arg Ala Val Val Trp Lys Asp Phe
1               5                   10                  15

Leu Gly Val Asn Ala Gln Phe Leu Trp Phe Ser Pro Glu Arg Tyr Asn
            20                  25                  30

Lys Gln Ile Asp Arg Leu Gln Asp Leu Gly Leu Glu Trp Val Arg Leu
        35                  40                  45

Asp Leu His Trp Asp Arg Leu Glu Thr Ala Glu Asp Gln Tyr Gln Leu
    50                  55                  60

Ala Ser Leu Asp Gln Leu Val Lys Asp Leu Glu Ala Arg Gln Leu Lys
65                  70                  75                  80

Ser Val Phe Tyr Leu Val Gly Ser Ala Arg Phe Ile Thr Thr Ala Pro
                85                  90                  95

Phe Tyr Ser Pro Phe Gln Asp Gln Tyr Pro Pro Arg Asp Pro Glu Val
            100                 105                 110

Phe Ala Arg Arg Met Ala Met Leu Ser Gln Arg Tyr Pro Ser Val Ala
        115                 120                 125

Ala Trp Gln Val Trp Asn Glu Pro Asn Leu Ile Gly Phe Trp Arg Pro
    130                 135                 140

Lys Ala Asp Pro Glu Gly Tyr Ala Lys Leu Leu Gln Ala Ser Thr Ile
145                 150                 155                 160

Ala Leu Arg Met Val Asp Pro Glu Lys Pro Val Val Ser Ala Gly Met
                165                 170                 175

Ala Phe Phe Ser Glu Met Pro Asp Gly Arg Thr Met Phe Asp Ala Leu
            180                 185                 190

Gly His Leu Gly Val Glu Ser Leu Gly Thr Ile Ala Thr Tyr His Pro
        195                 200                 205

Tyr Thr Gln Leu Pro Glu Gly Asn Tyr Pro Trp Asn Leu Asp Phe Val
    210                 215                 220
```

```
                        -continued

Ser His Ala Asn Gln Ile Asn Arg Ala Leu Arg Asn Ala Gly Val Pro
225             230                 235                 240

Ala Ile Trp Ser Thr Glu Trp Gly Trp Ser Ala Tyr Lys Gly Pro Lys
                245                 250                 255

Glu Leu Gln Asp Ile Ile Gly Val Glu Gly Gln Ala Asp Tyr Val Leu
            260                 265                 270

Arg Arg Leu Ala Leu Met Ser Ala Leu Asp Tyr Asp Arg Ile Phe Leu
        275                 280                 285

Phe Thr Leu Ser Asp Leu Asp Gln Arg Ala Ser Val Arg Asp Arg Asp
    290                 295                 300

Tyr Gly Leu Leu Asp Leu Asp Ala Asn Pro Lys Pro Val Tyr Leu Ala
305                 310                 315                 320

Leu Gln Arg Phe Leu Lys Val Thr Gly Pro Lys Leu Arg Pro Ala Asp
                325                 330                 335

Pro Pro Val Thr Glu Asp Leu Pro Asp Gly Ser Phe Ser Ile Gly Trp
            340                 345                 350

Thr Arg Glu Asp Gly Arg Asn Val Trp Leu Phe Trp Ser Ala Arg Gly
        355                 360                 365

Gly Asn Val Arg Leu Pro Lys Leu Lys Glu Ala Thr Leu His Asp Pro
    370                 375                 380

Leu Ser Gly Lys Val Thr Pro Leu Ser Gly Ser Asp Gly Leu Glu Val
385                 390                 395                 400

Pro Val Lys Ser Ser Leu Gln Met Leu Val Trp Glu
                405                 410
```